United States Patent
Strassner et al.

(10) Patent No.: US 11,771,432 B2
(45) Date of Patent: Oct. 3, 2023

(54) STAPLING AND CUTTING TO DEFAULT VALUES IN THE EVENT OF STRAIN GAUGE DATA INTEGRITY LOSS

(71) Applicant: Covidien LP, Mansfield, MA (US)

(72) Inventors: Haley E. Strassner, Hamden, CT (US); Alexander J. Hart, Tolland, CT (US); Charles R. Kollar, Washington, DC (US); James P. Delbo, North Haven, CT (US); Steven H. Joyce, Durham, CT (US)

(73) Assignee: Covidien LP, Mansfield, MA (US)

( * ) Notice: Subject to any disclaimer, the term of this patent is extended or adjusted under 35 U.S.C. 154(b) by 163 days.

(21) Appl. No.: 17/361,591

(22) Filed: Jun. 29, 2021

(65) Prior Publication Data

US 2022/0409208 A1    Dec. 29, 2022

(51) Int. Cl.
*A61B 17/115* (2006.01)
*A61B 17/068* (2006.01)
*A61B 17/072* (2006.01)
*A61B 90/00* (2016.01)
*A61B 17/3205* (2006.01)
*A61B 17/00* (2006.01)

(52) U.S. Cl.
CPC ....... *A61B 17/1155* (2013.01); *A61B 17/3205* (2013.01); *A61B 2017/00075* (2013.01); *A61B 2017/00398* (2013.01); *A61B 2090/065* (2016.02)

(58) Field of Classification Search
CPC .............. A61B 17/1155; A61B 17/105; A61B 17/11114; A61B 17/07292; A61B 17/068
See application file for complete search history.

(56) References Cited

U.S. PATENT DOCUMENTS

| | | | |
|---|---|---|---|
| 37,165 A | 12/1862 | Gary | |
| 3,209,754 A | 10/1965 | Brown | |
| 3,273,562 A | 9/1966 | Brown | |
| 3,499,591 A | 3/1970 | Green | |
| 3,528,693 A | 9/1970 | Pearson et al. | |

(Continued)

FOREIGN PATENT DOCUMENTS

| | | |
|---|---|---|
| CN | 101683284 A | 3/2010 |
| CN | 102648864 A | 8/2012 |

(Continued)

OTHER PUBLICATIONS

Detemple, P., "Microtechnology in Modern Health Care", Med Device Technol. 9(9):18-25 (1998).

(Continued)

*Primary Examiner* — Nathaniel C Chukwurah
(74) *Attorney, Agent, or Firm* — Carter, DeLuca & Farrell LLP

(57) ABSTRACT

A powered surgical device includes a power source and a motor coupled to the power source. The device may also include a transmission assembly movable by the motor. The device may also include a sensor configured to monitor operation of the transmission assembly and output sensor data. The device may also include a controller configured to: determine position of the transmission assembly and operate the motor based on the position of the transmission assembly and an interruption in the sensor data.

20 Claims, 11 Drawing Sheets

(56) References Cited

U.S. PATENT DOCUMENTS

| | | |
|---|---|---|
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Mien et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Foung et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |

(56) References Cited

U.S. PATENT DOCUMENTS

| | | |
|---|---|---|
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |

(56) References Cited

U.S. PATENT DOCUMENTS

| | | |
|---|---|---|
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0095067 A1* | 4/2011 | Ohdaira ............ A61B 17/07207 606/49 |
| 2011/0168757 A1 | 7/2011 | Viola et al. |

(56) References Cited

U.S. PATENT DOCUMENTS

| | | |
|---|---|---|
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2014/0309666 A1* | 10/2014 | Shelton, IV ......... A61B 17/072 606/139 |
| 2017/0095252 A1* | 4/2017 | Smith ................. A61B 17/1114 |
| 2019/0200997 A1* | 7/2019 | Shelton, IV ........... G16H 40/63 |
| 2019/0261991 A1* | 8/2019 | Beckman ............. A61B 17/068 |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |
| WO | 2020014056 A1 | 1/2020 |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM"; IC-On-Line, Electronic Component Manufacturers, pp. 1-2; Aug. 2013.

International Search Report and Written Opinion of the International Searching Authority issued in corresponding application PCT/IB2022/055934 dated Oct. 7, 2022 (12 pages).

* cited by examiner

STAPLING AND CUTTING TO DEFAULT VALUES IN THE EVENT OF STRAIN GAUGE DATA INTEGRITY LOSS

BACKGROUND

1. Technical Field

The present disclosure relates to surgical devices. More specifically, the present disclosure relates to handheld electromechanical surgical systems for performing surgical procedures.

2. Background of Related Art

Circular staplers are used in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another, and staples are ejected from the cartridge assembly toward the anvil assembly to form the staples in tissue to affect an end-to-end anastomosis, and an annular knife is advanced to core a portion of the clamped tissue portions. After the end-to-end anastomosis has been affected, the circular stapling apparatus is removed from the surgical site.

Powered surgical staplers have been developed and utilize one or more motors to clamp, cut, and staple tissue. These staplers also include one or more sensors, which provide feedback used in controlling the motors. If the sensor feedback is lost during one of the steps (e.g., stapling), conventional powered staplers may need to abort the process, which can result in a potentially dangerous situation where the stapler is stuck with the tissue clamped in the stapler. Recovery of the stapler may result in a loss of tissue and may prevent forming of an anastomosis at that site, especially in cases where there is a limited amount of tissue.

SUMMARY

The present disclosure provides a powered stapler having a strain gauge sensor configured to monitor forces during a stapling process ejecting a plurality of staples and/or a cutting processing advancing a knife to sever stapled tissue. If the strain gauge fails during the stapling process the powered stapler is configured to complete the stapling process and transition to a cutting process. In particular, if the strain gauge fails once stapling process has reached a point where aborting staples ejection is more dangerous than continuing without strain gauge feedback. A staple driver is moved to a default staple position, which is determined based on a lumen size being stapled and an offset factor, which is based on a variable force that is also dependent on the lumen size. Once the stapling process is completed, the powered stapler enters the cutting process, which moves a knife assembly to a default distance based on a tissue gap. The default cutting process is performed at a set, slower revolutions to prevent damage to the powered stapler and to minimize tissue pressure against the cutting assembly.

According to one embodiment of the present disclosure, a powered surgical device is disclosed. The surgical device includes a power source and a motor coupled to the power source. The device may also include a transmission assembly movable by the motor. The device may also include a sensor configured to monitor operation of the transmission assembly and output sensor data. The device may also include a controller configured to: determine position of the transmission assembly and operate the motor based on the position of the transmission assembly and an interruption in the sensor data.

Implementations of the above embodiment may include one or more of the following features. According to one aspect of the above embodiment, the controller may be further configured to: operate the motor to complete a process in response to the position of the transmission assembly being at or beyond a threshold position. The controller may be further configured to operate the motor to terminate a process in response to the position of the transmission assembly being below the threshold position and the interruption in the sensor data. The surgical device may include a reload configured to selectively couple to the transmission assembly. The reload may include a plurality of staples ejectable from the reload by the transmission assembly. The reload further may include a cutting assembly. Completing the process may include advancing the transmission assembly and at least one of ejecting the plurality of staples or advancing the cutting assembly. Terminating the process may include retracting the transmission assembly. The sensor may include a strain gauge, which may be configured to measure force imparted on the transmission assembly.

According to another embodiment of the present disclosure, a powered surgical device is disclosed. The surgical device may include a power source and a motor coupled to the power source. The device may also include a reload having a plurality of staples ejectable from the reload and a cutting assembly. The device may also include a stapling transmission assembly movable by the motor to eject the plurality of staples. The device may also include a cutting transmission assembly movable by the motor to advance the cutting assembly. The device may further include a sensor configured to monitor operation of the stapling transmission assembly and the cutting transmission assembly and to output sensor data. The device may also include a controller configured to: determine position of the stapling transmission assembly and the cutting transmission assembly. The controller may be also configured to operate the motor to move the stapling transmission assembly based on the position of the stapling transmission assembly and an interruption in the sensor data. The controller may be further configured to operate the motor to move the cutting transmission assembly based on the position of the cutting transmission assembly and an interruption in the sensor data.

Implementations of the above embodiment may include one or more of the following features. According to one aspect of the above embodiment, the controller may be further configured to operate the motor to complete a stapling process in response to the position of the stapling transmission assembly being at or beyond a threshold position. Completing the process may include advancing the stapling transmission assembly to eject the plurality of staples. The controller may be further configured to operate the motor to terminate the stapling process in response to the position of the stapling transmission assembly being below the threshold position and the interruption in the sensor data. Terminating the process may include retracting the stapling transmission assembly. The controller may be further configured to operate the motor to complete a cutting process in response to the position of the cutting transmission assembly being at or beyond a threshold position. Completing the process may include advancing the cutting transmission assembly to advance the cutting assembly. The controller may be further configured to operate the motor to terminate the cutting process in response to the position of the cutting transmission assembly being below the threshold position and the interruption in the sensor data. Terminating the process may include retracting the cutting transmission assembly. The sensor may include a strain gauge. The strain gauge is configured to measure force imparted on the stapling transmission assembly and the cutting transmission assembly.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
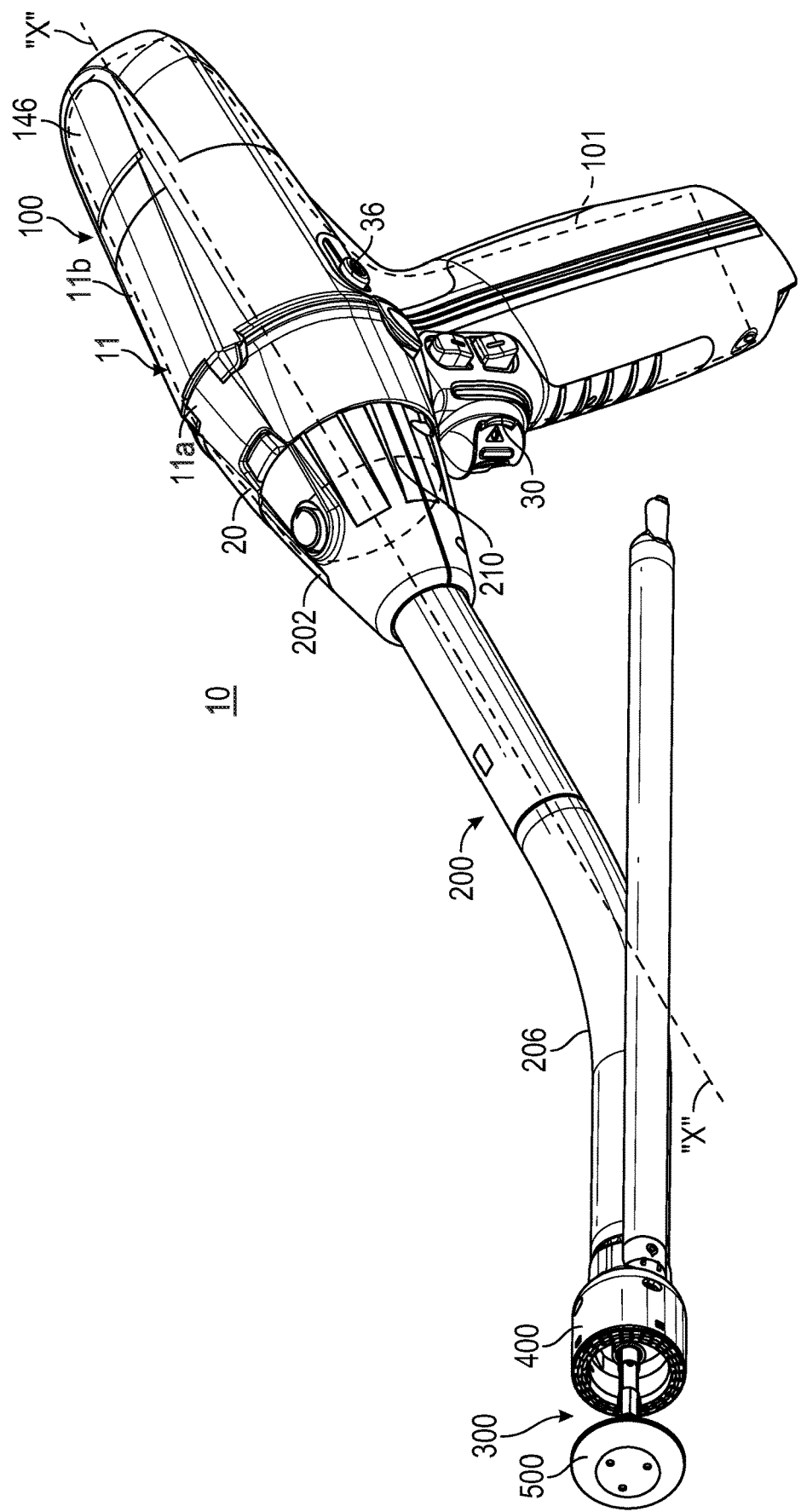
FIG. 1 is a perspective view of a powered circular stapler including a handle assembly, an adapter assembly, and an end effector, according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered circular stapler 10 having a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation.

FIG. 1 illustrates a surgical device, such as, for example, a powered circular stapler 10 for forming end-to-end anastomosis ("EEA"), including a handle assembly 100, which is configured for selective connection with an adapter assembly 200. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 and an outer shell housing 11 configured to selectively receive and encase power handle 101. The shell housing 11 includes a distal half-section 11a and a proximal half-section 11b pivotably connected to distal half-section 11a. When joined, distal and proximal half-sections 11a, 11b define a shell cavity therein in which power handle 101 is disposed.

While the powered circular stapler 10 is described herein as a modular device including a plurality of interconnected components, such as the handle assembly 100, the removable shell housing 11, and the adapter assembly 200, etc. The powered circular stapler 10 may be formed as an integrated device with one or more of the components being securely attached to each other, e.g., during manufacturing of the powered circular stapler.

Distal and proximal half-sections 11a, 11b of shell housing 11 are divided along a plane that traverses a longitudinal axis "X" of adapter assembly 200. Distal half-section 11a of shell housing 11 defines a connecting portion 20 configured to accept a corresponding drive coupling assembly 210 (FIG. 3) of adapter assembly 200. Distal half-section 11a of shell housing 11 supports a toggle control button 30. Toggle control button 30 is capable of being actuated in four directions (e.g., a left, right, up and down).

Figure 2:
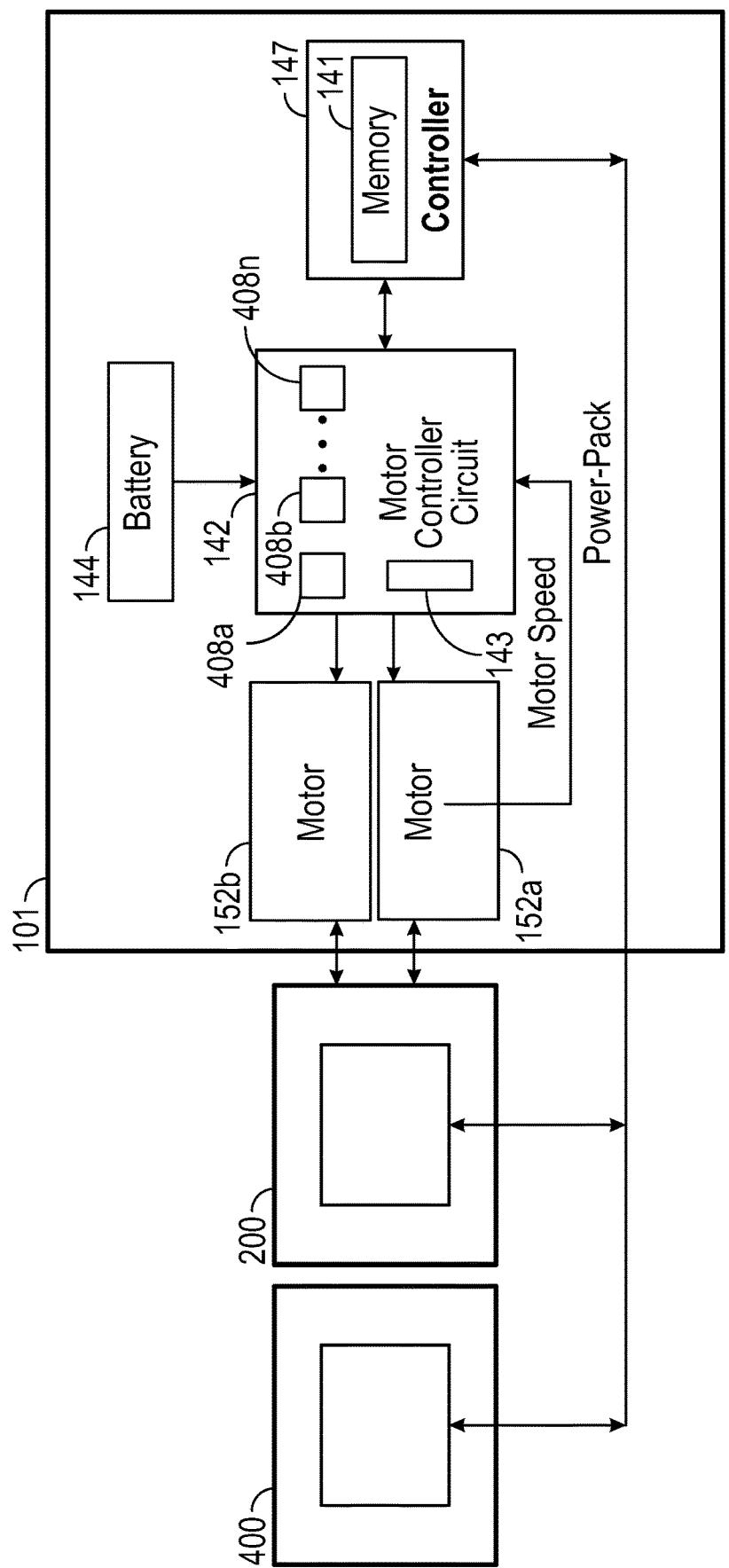
FIG. 2 is a schematic diagram of the handle assembly, the adapter assembly, and the end effector of FIG. 1.

With reference to FIGS. 1 and 2, the power handle 101 includes a main controller circuit board 142, a rechargeable battery 144 configured to supply power to any of the electrical components of handle assembly 100, and a plurality of motors, i.e., a first motor 152a, a second motor 152b coupled to the battery 144. The power handle 101 also includes a display 146. In embodiments, the motors 152a and 152b may be coupled to any suitable power source configured to provide electrical energy to the motors 152a and 152b, such as an AC/DC transformer. Each of the motors 152a and 152b is coupled a motor controller 143 which controls the operation of the corresponding motors 152a and 152b including the flow of electrical energy from the battery 144 to the motors 152a and 152b. A main controller 147 is provided that controls the power handle 101. The main controller 147 is configured to execute software instructions embodying algorithms disclosed herein, such as clamping, stapling, and cutting algorithms which control operation of the power handle 101.

The motor controller 143 includes a plurality of sensors 408a . . . 408n configured to measure operational states of the motors 152a and 152b and the battery 144. The sensors 408a-n include a strain gauge 408b and may also include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motors 152a and 152b. The sensor 408a also includes an encoder configured to count revolutions or other indicators of the motors 152a and 152b, which is then use by the main controller 147 to calculate linear movement of components movable by the motors 152a and 152b. Angular velocity may be determined by measuring the rotation of the motors 152a and 152b or a drive shaft (not shown) coupled thereto and rotatable by the motors 152a and 152b. The position of various axially movable drive shafts may also be determined by using various linear sensors disposed in or in proximity to the shafts or extrapolated from the RPM measurements. In embodiments, torque may be calculated based on the regulated current draw of the motors 152a and 152b at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motors 152a and 152b.

The motor controller 143 is coupled to the main controller 147, which includes a plurality of inputs and outputs for interfacing with the motor controller 143. In particular, the main controller 147 receives measured sensor signals from the motor controller 143 regarding operational status of the motors 152a and 152b and the battery 144 and, in turn, outputs control signals to the motor controller 143 to control the operation of the motors 152a and 152b based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408b of the adapter assembly 200 using a wired or a wireless connection and is configured to receive strain measurements from the strain gauge 408b which are used during operation of the power handle 101.

The power handle 101 includes a plurality of motors 152a and 152b each including a respective motor shaft (not explicitly shown) extending therefrom and configured to drive a respective transmission assembly. Rotation of the motor shafts by the respective motors function to drive shafts and/or gear components of adapter assembly 200 in order to perform the various operations of handle assembly 100. In particular, motors 152a and 152b of power handle 101 are configured to drive shafts and/or gear components of adapter assembly 200 in order to selectively extend/retract a trocar member 274 (FIG. 4) of a trocar assembly 270 of adapter assembly 200. Extension/retraction of the trocar member 274 opens/closes end effector 300 (when anvil assembly 500 is connected to trocar member 274 of trocar assembly 270), fire an annular array of staples 423 of reload 400, and move an annular knife 444 of reload 400.

The reload 400 includes a storage device 402 configured to store operating parameters of the reload 400 including starting clamping force, maximum clamping force, a force factor, and the like. Each type of reload 400 may have a corresponding starting clamping force, which the main controller 147 may obtain automatically by reading the starting clamping force value from the storage device 402 and/or set manually by the user by selecting either the type of the reload 400 or the clamping force directly. Starting clamping force may be any suitable threshold from about 100 pounds to about 200 pounds, in embodiments, the target clamping force may be approximately 150 pounds. In embodiments, a 33 mm sized reload 400 may have a clamping force of about 150 lbs.

Figure 3:
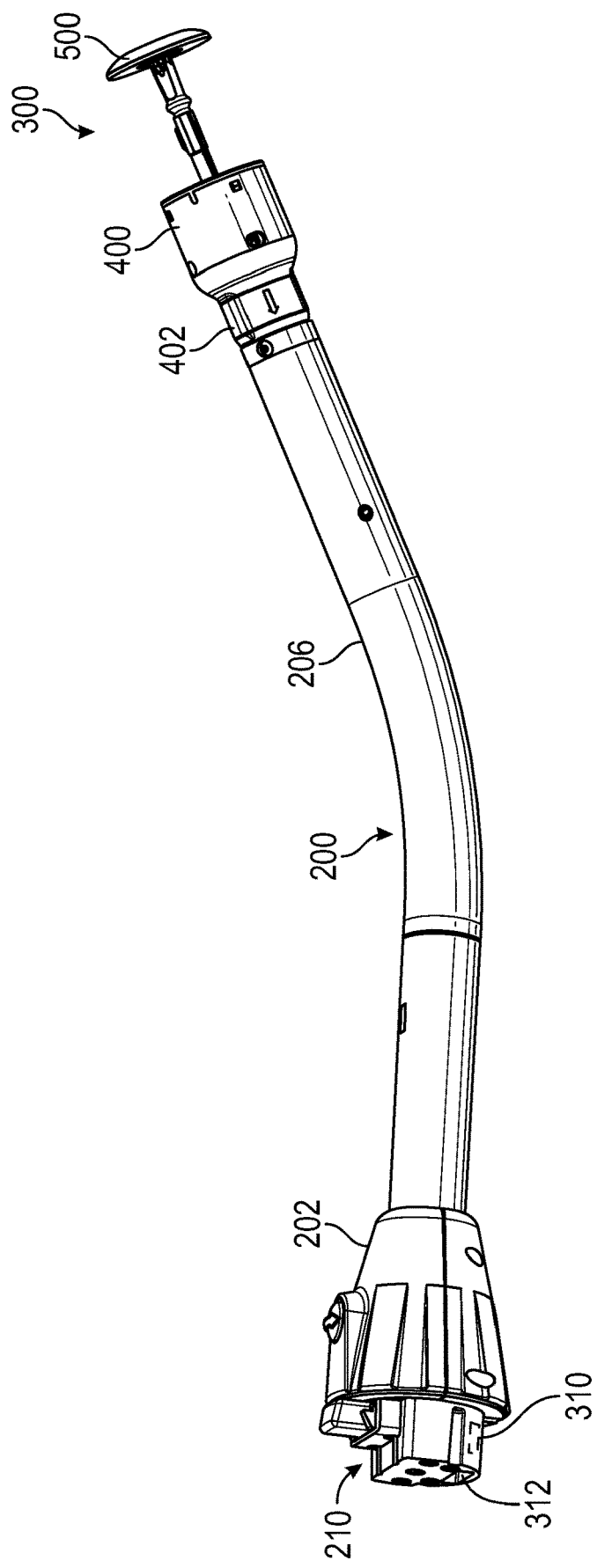
FIG. 3 is a side perspective view of the adapter assembly and the end effector, an annular reload and an anvil assembly, attached to the adapter assembly of FIG. 1 according to an embodiment of the present disclosure.
Figure 4:
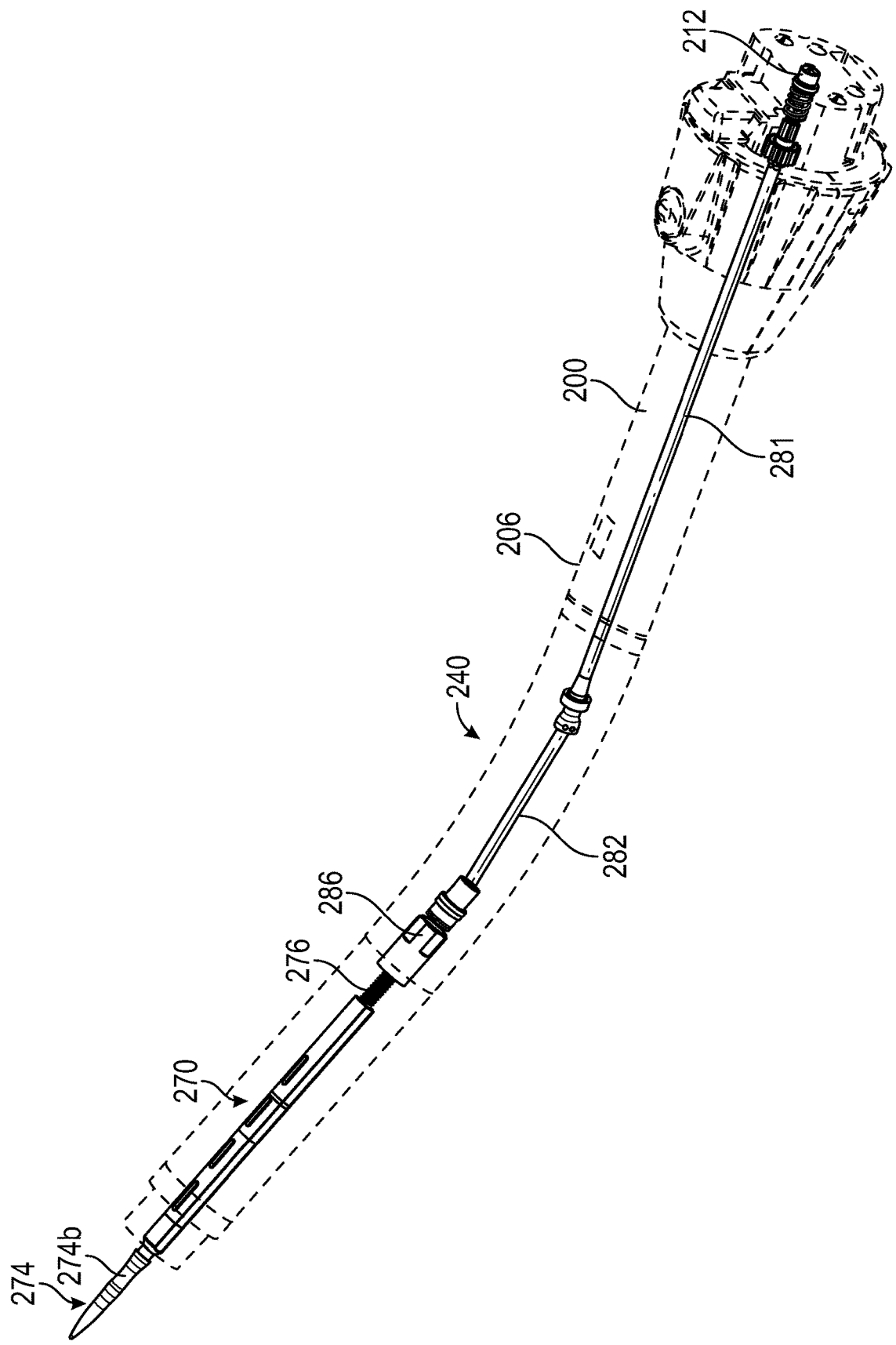
FIG. 4 is a perspective view of a clamping transmission assembly disposed within the adapter assembly of FIG. 1, shown partially in phantom.

Turning now to FIGS. 3 and 4, adapter assembly 200 includes an outer knob housing 202 and an outer tube 206 extending from a distal end of knob housing 202. Knob housing 202 and outer tube 206 are configured and dimensioned to house the components of adapter assembly 200. The knob housing 202 includes an electrical connector 312 and a storage device 310 coupled thereto. The storage device 310 is configured to store various operating parameters pertaining to the adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver 430 or knife assembly 440 of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274b of trocar member 274 is configured to selectively engage anvil assembly 500, such that axial movement of trocar member 274, via a rotation of drive screw 276, results in a concomitant axial movement of anvil assembly 500.

With reference to FIG. 4, a clamping transmission assembly 240 includes first rotatable proximal drive shaft 212 coupled to one of the motors 152a and 152b, a second rotatable proximal drive shaft 281, a rotatable distal drive shaft 282, and a coupling member 286, each of which are supported within the outer tube 206 of adapter assembly 200. Clamping transmission assembly 240 functions to extend/retract trocar member 274 of trocar assembly 270 of adapter assembly 200, and to open/close the anvil assembly 510 when anvil assembly 510 is connected to trocar member 274.

Figure 5:
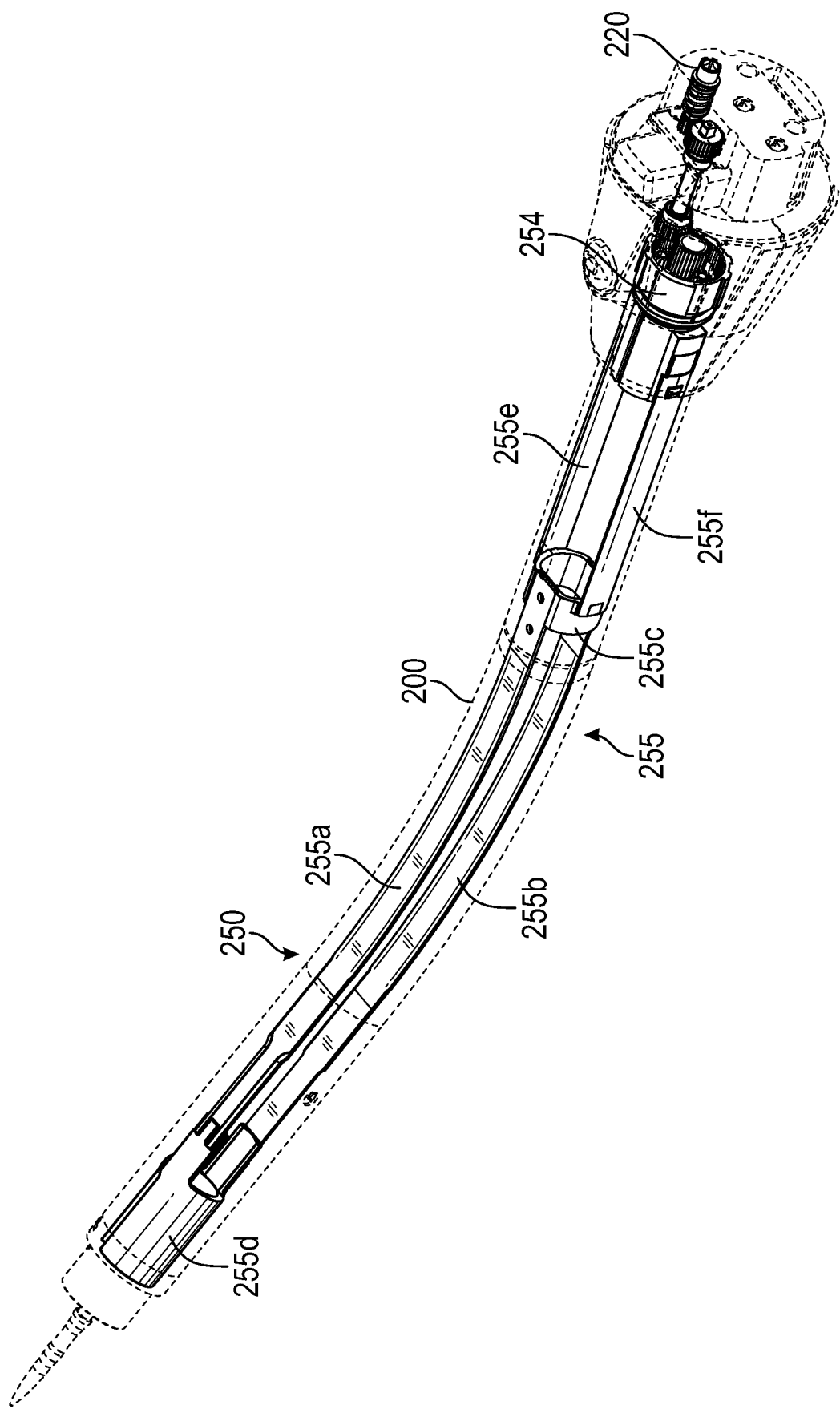
FIG. 5 is a perspective view of a stapling transmission assembly disposed within the adapter assembly of FIG. 1, shown partially in phantom.
Figure 6:
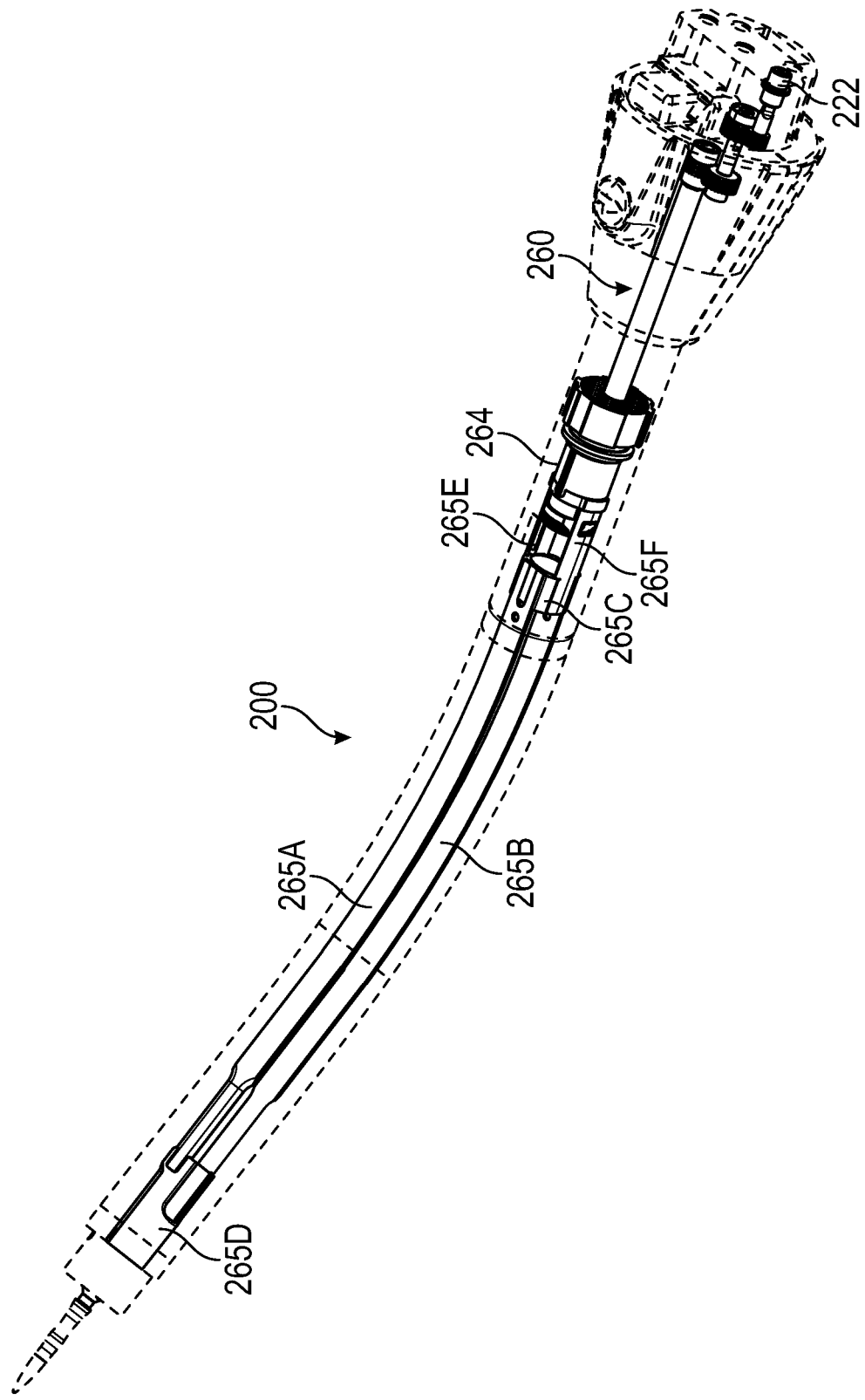
FIG. 6 is a perspective view of a cutting transmission assembly disposed within the adapter assembly of FIG. 1, shown partially in phantom.

With reference to FIG. 5, the adapter assembly 200 includes a stapling transmission assembly 250 for interconnecting the first motor 152a and a second axially translatable drive member of reload 400, wherein the stapling transmission assembly 250 converts and transmits a rotation of the first motor 152a to an axial translation of an outer flexible band assembly 255 of adapter assembly 200, and in turn, the staple driver 430 of reload 400 to fire staples 423 from the reload 400 and against anvil assembly 510.

The stapling transmission assembly 250 of adapter assembly 200 includes the outer flexible band assembly 255 secured to staple driver coupler 254. A second rotatable proximal drive shaft 220 is coupled to the second motor 152b and is configured to actuate that staple driver coupler 254, which converts rotational movement into longitudinal movement. Outer flexible band assembly 255 includes first and second flexible bands 255a, 255b laterally spaced and connected at proximal ends thereof to a support ring 255c and at distal ends thereof to a proximal end of a distal pusher 255d. Each of first and second flexible bands 255a, 255b is attached to support ring 255c and distal pusher 255d. Outer flexible band assembly 255 further includes first and second connection extensions 255e, 255f extending proximally from support ring 255c. First and second connection extensions 255e, 255f are configured to operably connect outer flexible band assembly 255 to staple driver coupler 254 of stapling transmission assembly 250.

The adapter assembly 200 also includes a cutting transmission assembly 260 for interconnecting the second motor 152b and the annular knife 444 of reload 400, wherein the cutting transmission assembly 260 converts and transmits a rotation of one of the second motor 152b to an axial translation of an outer flexible band assembly 265 of adapter assembly 200, and in turn, a knife carrier 442 of reload 400 to advance the annular knife 444 from the reload 400 and against anvil assembly 510.

Inner flexible band assembly 265 includes first and second flexible bands 265a, 265b laterally spaced and connected at proximal ends thereof to a support ring 265c and at distal ends thereof to a proximal end of a support base 265d. Each of first and second flexible bands 265a, 265b are attached to support ring 265c and support base 265d.

Inner flexible band assembly 265 further includes first and second connection extensions 265e, 265f extending proximally from support ring 265c. First and second connection extensions 265e, 265f are configured to operably connect inner flexible band assembly 265 to knife driver 264 of cutting transmission assembly 260. Support base 265d extends distally from flexible bands 265a, 265b and is configured to connect with a knife assembly 440 of reload 400.

Figure 7:
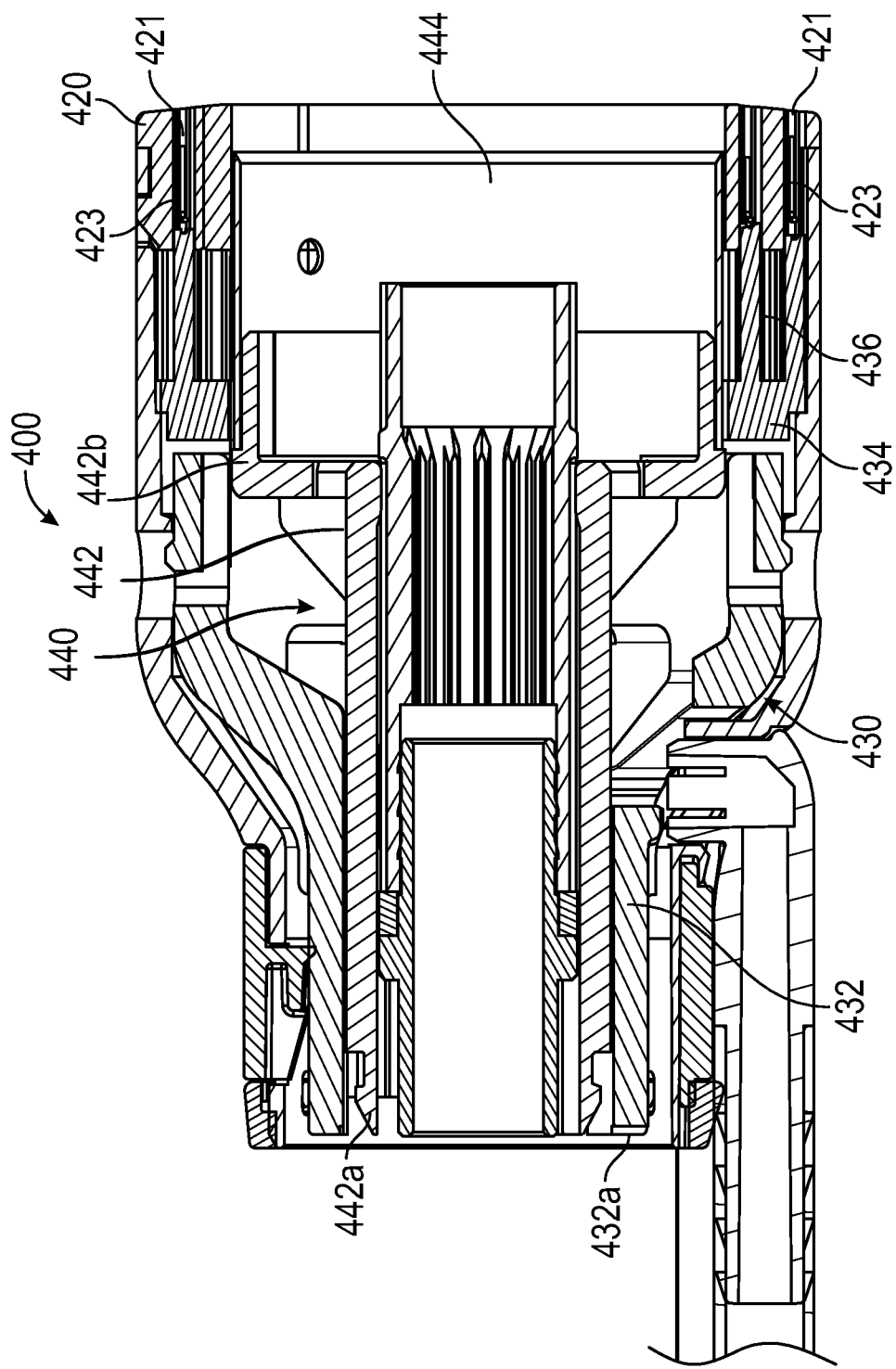
FIG. 7 is a cross-sectional view of a reload of the end effector of FIG. 1.

With reference to FIG. 7, staple driver 430 of reload 400 includes a staple cartridge 420 having a driver adapter 432 and a driver 434. A proximal end 432a of driver adapter 432 is configured for selective contact and abutment with distal pusher 255d of outer flexible band assembly 255 of stapling transmission assembly 250 of adapter assembly 200. In operation, during distal advancement of outer flexible band assembly 255, as described above, distal pusher 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples 423. Accordingly, advancement of driver 434 relative to staple cartridge 420 causes ejection of the staples 423 from staple cartridge 420.

The knife assembly 440 of the reload 400 includes a knife carrier 442 and an annular knife 444 secured about a distal end 442b of knife carrier 442. A proximal end 442a of knife carrier 442 is configured to engage the support base 265d of inner flexible band assembly. In operation, during distal advancement of inner flexible band assembly 265, support base 265d of inner flexible band assembly 265 connects with proximal end 442a of knife carrier 442 to advance knife carrier 442 and annular knife 444 from a first or proximal position to a second or advanced position to cause the cutting of tissue disposed between staple cartridge 420 and anvil assembly 510.

Forces during an actuation of trocar member 274, closing of end effector 300 (e.g., a retraction of anvil assembly 500 relative to reload 400), ejecting staples 423 from the reload 400, and advancement of the knife assembly 440 may be measured by the strain gauge 408b in order to monitor and control various processes, such as firing of staples 423 from reload 400; monitor forces during a firing and formation of the staples 423 as the staples 423 are being ejected from reload 400; optimize formation of the staples 423 (e.g., staple crimp height) as the staples 423 are being ejected from reload 400 for different indications of tissue; and monitor and control a firing of the annular knife of reload 400.

Figure 8:
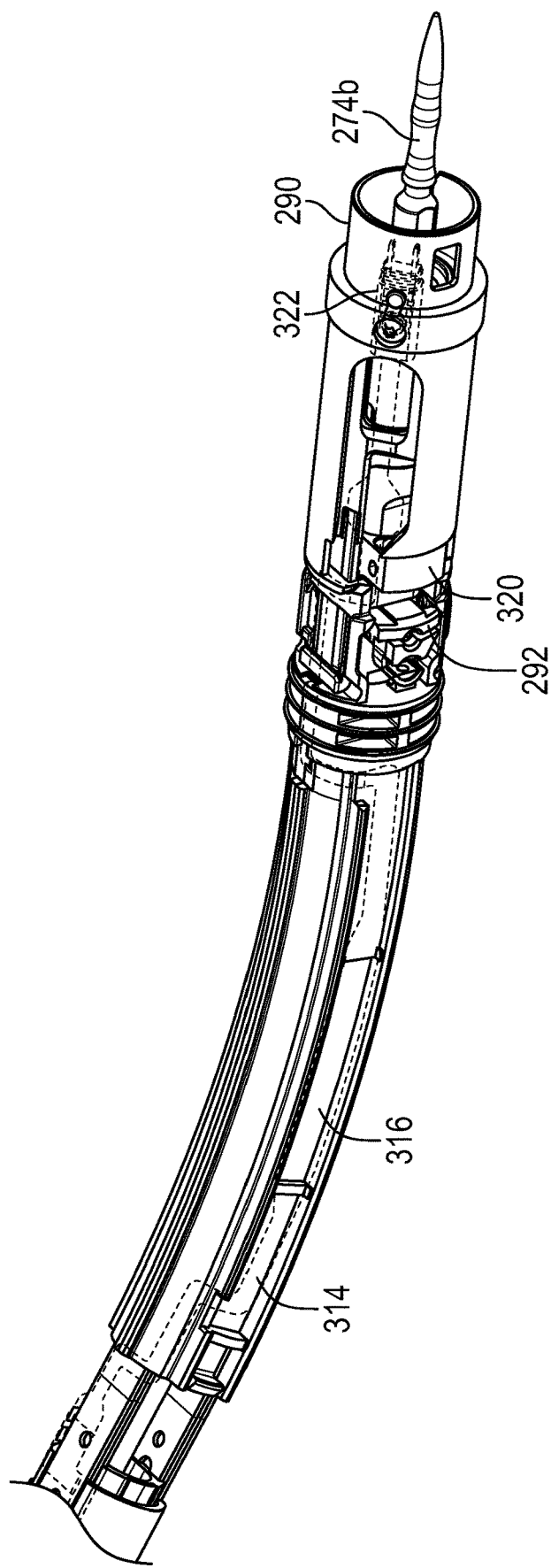
FIG. 8 is a perspective view of the adapter assembly, shown partially disassembled, with a strain gauge assembly.

With reference to FIG. 8, the strain gauge 408b of adapter assembly 200 is disposed within a strain gauge housing 320. The strain gauge 408b measures and monitors the retraction of trocar member 274 as well as the ejection and formation of the staples 423 from the reload 400. During the closing of end effector 300, when anvil assembly 500 contacts tissue, an obstruction, a tissue-contacting surface of the reload 400, staple ejection, or the like, a reaction force is exerted on anvil assembly 500 which is in a generally distal direction. This distally directed reaction force is communicated from anvil assembly 500 to the strain gauge 408b. The strain gauge 408b then communicates signals to main controller circuit board 142 of power handle 101 of handle assembly 100. Graphics (FIG. 8) are then displayed on the display 146 of handle assembly 100 to provide the user with real-time information related to the status of the firing of handle assembly 100.

The trocar assembly 270 is axially and rotationally fixed within outer tube 206 of adapter assembly 200. With reference to FIG. 8, adapter assembly 200 includes a support block 292 fixedly disposed within outer tube 206. The strain gauge housing 320 is disposed between the support block 292 and a connector sleeve 290. The reload 400 is removably coupled to the connector sleeve 290.

In operation, strain gauge 408b of adapter assembly 200 measures and monitors the retraction of trocar member 274, which passes through the strain gauge 408b. The strain gauge 408b of adapter assembly 200 also measures and monitors ejection of the staples 423 from the reload 400, since the first and second flexible bands 255a, 255b also pass through the strain gauge 408b. During clamping, stapling and cutting, a reaction force is exerted on anvil assembly 500 and the reload 400, which is communicated to support block 292, which then communicates the reaction force to a strain sensor of the strain gauge 408b.

Strain sensor of strain gauge 408b may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge 408b provides a closed-loop feedback to a firing/clamping load exhibited by first, second and third force/rotation transmitting/converting assemblies.

Strain sensor of strain gauge 408b then communicates signals to main controller circuit board 142. Graphics are then displayed on display 146 of power-pack core assembly 106 of handle assembly 100 to provide the user with real-time information related to the status of the firing of handle assembly 100. Strain gauge 408b is also electrically connected to the electrical connector 312 (FIG. 3) via proximal and distal harness assemblies 314, 316.

For further details regarding the construction and operation of the circular stapler and its components, reference may be made to International Application Publication No. PCT/US2019/040440, filed on Jul. 3, 2019, the entire contents of which being incorporated by reference herein.

During operation, the anvil assembly 500 (already positioned by surgeon) is attached to the trocar member 274 and the user begins the clamping process on the tissue interposed between reload 400 and the anvil assembly 500 by pressing on the bottom of the toggle control button 30. During clamping, the anvil assembly 500 is retracted toward the reload 400 until reaching a preset, fully clamped position, namely a position of the anvil assembly 500 at which the tissue is fully clamped between the anvil assembly 500 and the reload 400. The preset, fully clamped position varies for each of the different types of reloads. While clamping, the strain gauge 408b continuously provides measurements to the main controller 147 on the force imparted on the trocar member 274 as it moves the anvil assembly 500 to clamp tissue between the anvil assembly 500 and the reload 400.

The user commences a surgical procedure by positioning the adapter assembly 200, including the trocar member 274 and the anvil assembly 510, within the colorectal or upper gastrointestinal region. The user presses the toggle control button 30 to extend the trocar member 274 until it pierces tissue. After extension of the trocar member 274, the anvil assembly 510 that was previously positioned by surgeon is attached to the trocar member 274 and the user begins the clamping process on the tissue interposed between reload 400 and the anvil assembly 510 by pressing on the bottom portion of the toggle control button 30. Once clamping is successfully completed, the user initiates the stapling sequence.

To initiate stapling sequence, the user presses one of the safety buttons 36 of the power handle 101, which acts as a safety and arms the toggle control button 30, allowing it to commence stapling. Upon activation of the safety button 36, a rotation verification calibration check is performed. The display 146 transitions to the stapling sequence display, which includes a circle illustrating an animated view of a circular anastomosis, a progress bar, and a staple icon. The stapling sequence screen is displayed until user initiates the stapling sequence, exits the stapling sequence, or unclamps.

To commence the stapling sequence, the user presses down on the toggle control button 30, which moves the stapling transmission assembly 250 to convert rotation to linear motion and to eject and form staples 423 from circular reload 400. In particular, during the firing sequence, the first motor 152a advances the driver 434 using the stapling transmission assembly 250. The force imparted on the stapling transmission assembly 250 is monitored by the strain gauge 408b. The process is deemed complete once the stapling transmission assembly 250 reaches a target staple position corresponding to the staple stroke information stored on the storage device 402 of the reload 400 and a force compensation factor detected by the strain gauge 408b. This indicates that the staples 423 have been successfully ejected and deformed against the anvil assembly 510.

Figure 9:
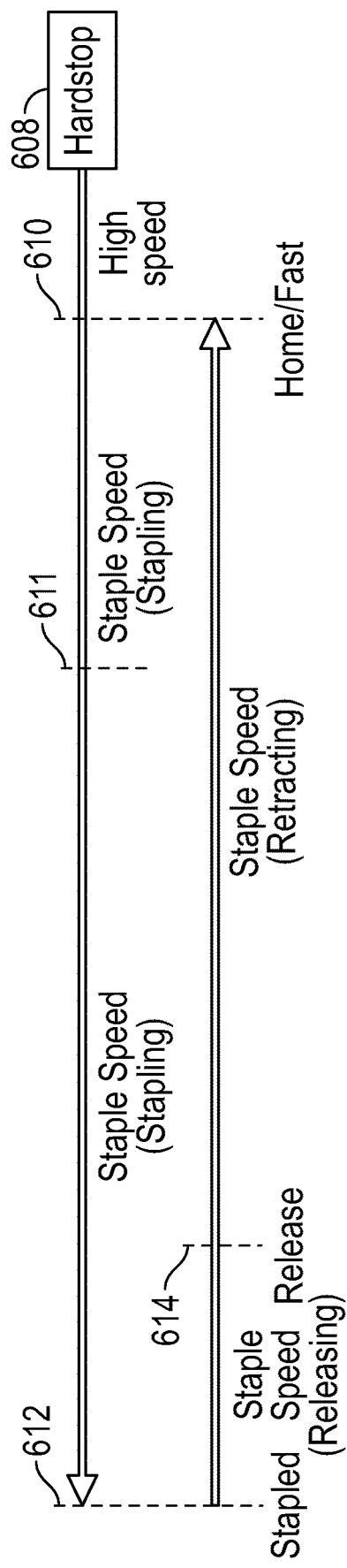
FIG. 9 is a schematic diagram illustrating travel distance and speed of the driver and a corresponding motor during a stapling sequence performed by the handheld surgical device of FIG. 1 according to an embodiment of the present disclosure.

With reference to FIG. 9, which schematically illustrates the travel distance and speed of the first motor 152a as it advances the driver 434 within the reload 400. The staple driver is initially advanced from a first position 608 (e.g., hardstop) at a first speed for a first segment from the first position 608 to a second position 610 (e.g., base position). From the second position 610, the driver 434 is advanced at a second speed, slower than the first speed, until it reaches a third position 612 (e.g., target staple position), to eject the staples 423.

After reaching the second position 610, the first motor 152a is operated at the second, slower speed to eject the staples 423 from the reload 400. During the second segment, as the staples 423 are ejected from the reload 400 to staple tissue, the main controller 147 continually monitors the strain measured by the strain gauge 408b and determines whether the force corresponding to the measured strain is between a minimum stapling force and a maximum stapling force. The stapling force range may be stored in the storage device 402 of the reload 400 and used by the main controller 147 during the stapling sequence. Determination whether the measured force is below the minimum stapling force is used to verify that the staples 423 are present in the reload 400. In addition, a low force may be also indicative of a failure of the strain gauge 408b. If the measured force is below the minimum stapling force, then the main controller 147 signals the first motor 152a to retract the driver 434 to the second position 610. The main controller 147 also displays a sequence on the display 146 instructing the user the steps to exit stapling sequence and retract the anvil assembly 510. After removing the anvil assembly 510, the user may replace the circular adapter assembly 200 and the reload 400 and restart the stapling process.

If the measured force is above the maximum stapling force, which may be about 580 lbs., the main controller 147 stops the first motor 152a and displays a sequence on the display 146 instructing the user the steps to exit the stapling sequence. However, the user may still continue the stapling process without force limit detection by pressing on the toggle control button 30.

The main controller 147 determines that the stapling process is completed successfully, if the first motor 152a reached a third position 612 associated with stapled tissue and during this movement the measured strain was within the minimum and maximum stapling force limits. Thereafter, the first motor 152a retracts the driver 434 to a fourth position 614 to release pressure on the tissue prior to starting the cutting sequence.

Figure 10:
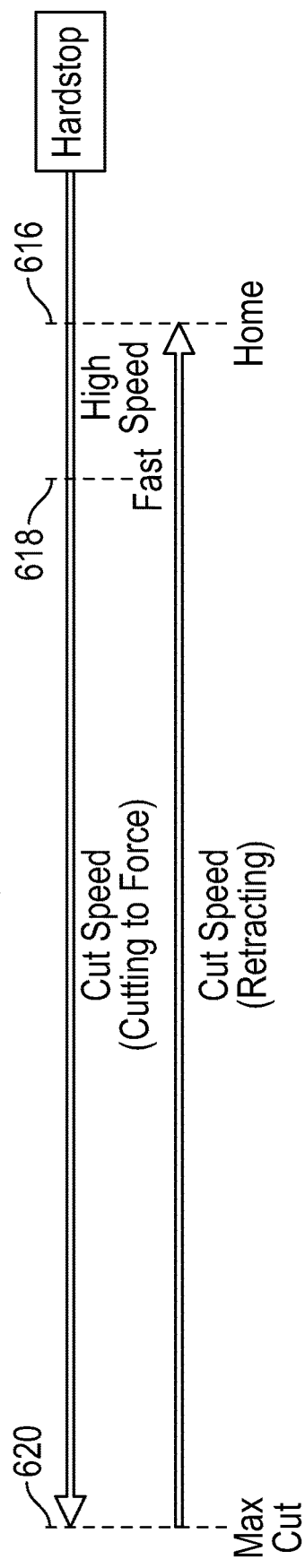
FIG. 10 is a schematic diagram illustrating travel distance and speed of the knife assembly and a corresponding motor during a cutting sequence performed by the handheld surgical device of FIG. 1 according to an embodiment of the present disclosure.

With reference to FIG. 10, which schematically illustrates the travel distance and speed of the second motor 152b as it advances the knife assembly 440. The knife assembly 440 is initially advanced from a first position 616 at a first speed for a first segment from the first position 616 until a second position 618. From the second position 618, the knife assembly 440 is advanced at a second speed, slower than the first speed, until it reaches a third position 620, to cut the stapled tissue.

During the first segment, the second motor 152b advances the knife assembly 440 until the knife assembly 440 contacts the stapled tissue. After reaching the second position 618, the third motor 154 is operated at the second, slower speed to cut the stapled tissue. As the knife assembly 440 is advanced to cut tissue, the main controller 147 continually monitors the strain measured by the strain gauge assembly 320 and determines whether the force corresponding to the measured strain is between a target cutting force and a maximum cutting force. The target cutting force and the maximum cutting force may be stored in the storage device 405 of the reload 400 and used by the main controller 147 during cutting sequence. If the target cutting force is not reached during the cutting sequence, which is indicative of improper cutting, then the main controller 147 signals the second motor 152b retract the knife assembly 440 allowing the user to open the reload 400 and abort the cutting sequence. The main controller 147 also displays a sequence on the display 146 indicating to the user the steps to exit the cutting sequence and retract the anvil assembly 510. After removing the anvil assembly 510, the user may replace the circular adapter assembly 200 and the reload 400 and restart the stapling process. If the measured force is above the maximum cutting force, the main controller 147 stops the second motor 152*b* and displays a sequence on the display 146 instructing the user to exit the cutting sequence.

Figure 11:
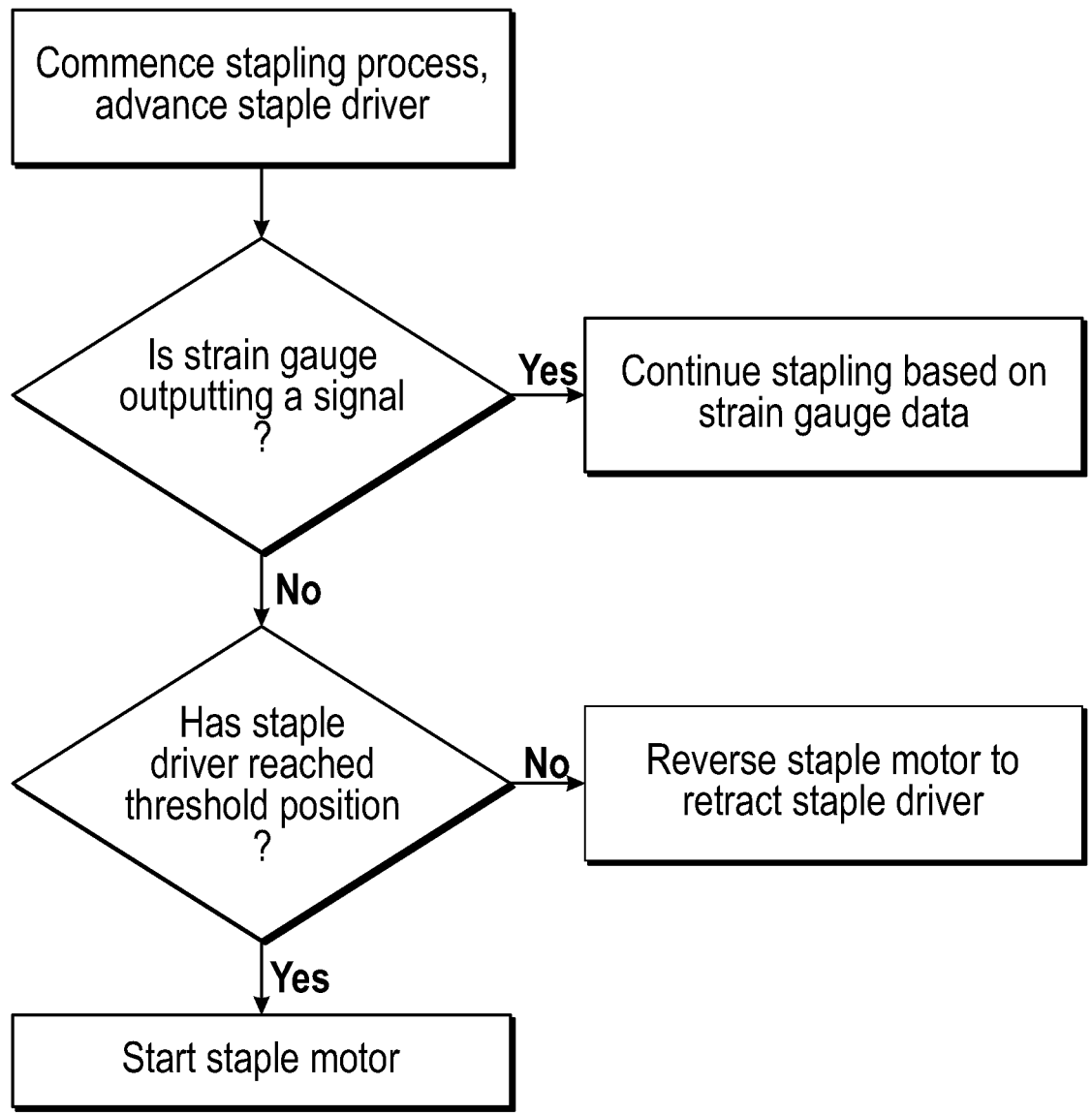
FIG. 11 is a flow chart of a method for controlling the powered circular stapler during the stapling process of FIG. 9 according to an embodiment of the present disclosure.
Figure 12:
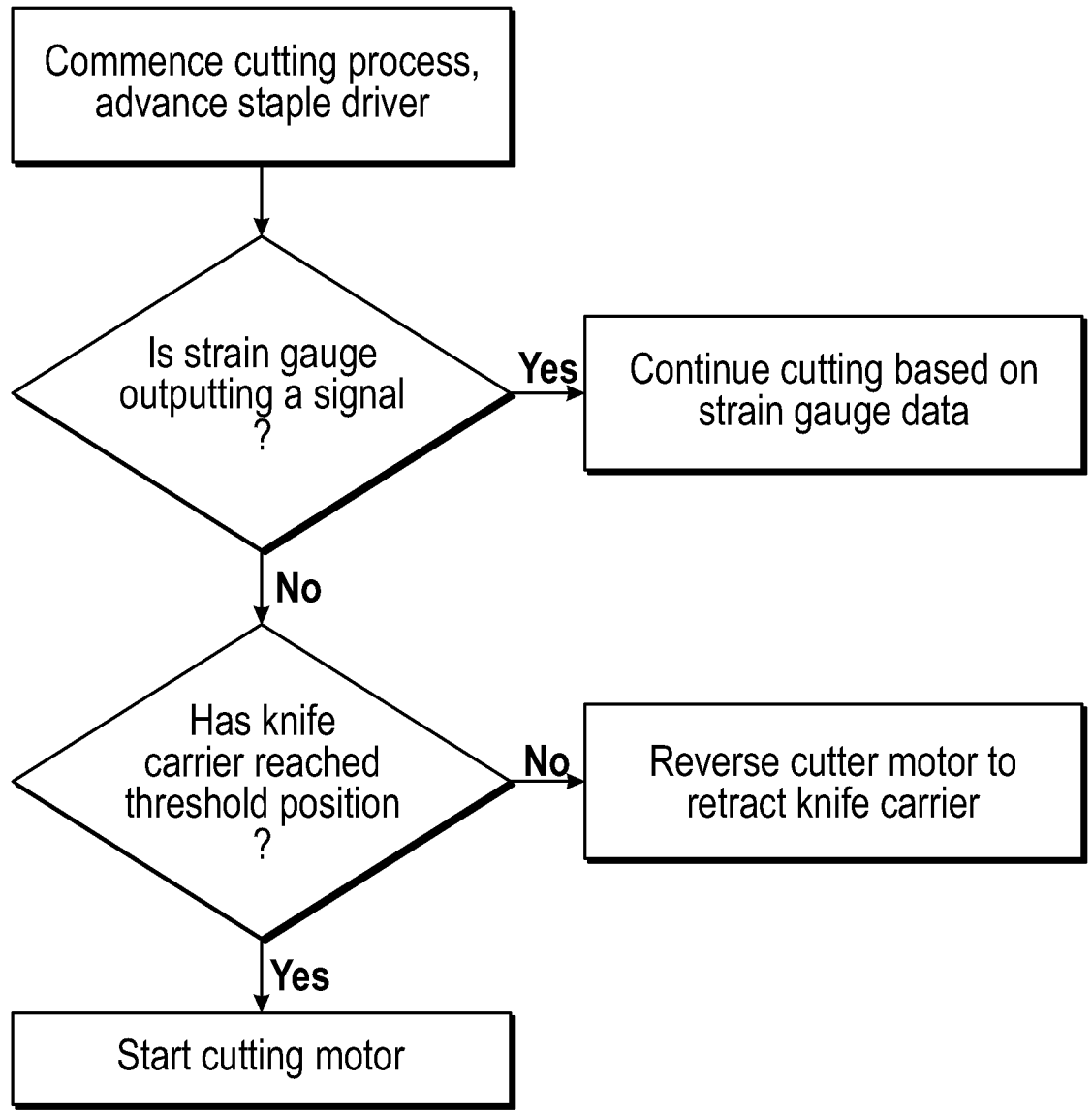
FIG. 12 is a flow chart of a method for controlling the powered circular stapler during the stapling process of FIG. 10 according to an embodiment of the present disclosure.

With reference to FIGS. 11 and 12, the powered circular stapler 10 is configured to operate during stapling and cutting processes in the event that the main controller 147 is no longer receiving data from the strain gauge 408*b*, e.g., due to failure of the strain gauge 408*b*, an input/output error between the strain gauge 408*b* and the main controller 147, etc. FIG. 10 illustrates a process for operating the powered circular stapler 10 during the stapling process if sensor data flow is interrupted. Initially, the stapling process is commenced by toggling the control button 30. Interruption in the sensor data may be defined as lack of sensor data for a predetermined period of time, i.e., from about 1 second to about 5 seconds, such that temporary interruptions do not trigger the main controller 147 to take remedial actions. During the stapling process, the main controller 147 continuously receives strain data from the strain gauge 408*b*. As used herein, "continuously" denotes sampling and/or polling of the strain gauge 408*b* at any suitable rate. If the data flow is uninterrupted, the main controller 147 continues the stapling process as described above with respect to FIG. 9. However, if the strain data flow is interrupted for any reason, the main controller 147 then verifies whether the staple driver 434 is at a threshold position 611, which is between the second position 612 and the third position 614. The threshold position 611 may be based on the size of the lumen, i.e., circumference of the reload 400, as well as sensor data collected during a tissue clamping process. Distance verification is based on distance data from an encoder or any other suitable position sensor. Thus, if the strain data flow is interrupted prior to the staple driver 434 reaching the threshold position 611, the stapling process is terminated and the staple driver 434 is retracted. However, if the strain data flow is interrupted while the staple driver 434 is being advanced from the threshold position 611 to the third position 614, then the main controller 147 continues the stapling process and the staple driver 434 is advanced in an uninterrupted manner. Once the staple driver 434 reaches the third position 612, the retraction process of the staple driver is performed as described above with respect to FIG. 9.

FIG. 12 illustrates a process for operating the powered circular stapler 10 during the cutting process if sensor data flow is disrupted. During the cutting process, just as during the stapling process, the main controller 147 continuously receives strain data from the strain gauge 408*b*. If the data flow is uninterrupted, the main controller 147 continues the cutting process as described above with respect to FIG. 10. However, if the strain data flow is interrupted for any reason, the main controller 147 then verifies whether the knife assembly 440 is at the second position 618 (e.g., base position), which corresponds to a threshold position. The threshold position may be based on the size of the lumen, i.e., circumference of the reload 400, as well as sensor data collected during a tissue clamping process. Thus, if the strain data flow is interrupted prior to the knife assembly 440 reaching or being at the threshold position, the cutting process is terminated and the knife assembly 440 is retracted. However, if the strain data flow is interrupted while the knife assembly 440 is being advanced from the second position 618 i.e., past the threshold position, to the third position 620 corresponding to cut completion, then the main controller 147 continues the cutting process and the knife assembly 440 is advanced in an uninterrupted manner. Once the knife assembly 440 reaches the third position 618, the retraction process is performed as described above with respect to FIG. 10. If the sensor data is interrupted during the stapling process, the cutting process may also be carried as described above. This allows for the stapling and cutting processes to be completed even in the event of sensor data interruption.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
   a power source;
   a motor coupled to the power source;
   a transmission assembly movable by the motor;
   a sensor configured to monitor operation of the transmission assembly and output sensor data;
   a controller configured to:
      determine position of the transmission assembly; and
      operate the motor based on the position of the transmission assembly and an interruption in the sensor data.

2. The surgical device according to claim 1, wherein the controller is further configured to:
   operate the motor to complete a process in response to the position of the transmission assembly being at or beyond a threshold position.

3. The surgical device according to claim 2, wherein the controller is further configured to:
   operate the motor to terminate a process in response to the position of the transmission assembly being below the threshold position and the interruption in the sensor data.

4. The surgical device according to claim 3, further comprising:

a reload configured to selectively couple to the transmission assembly, the reload including a plurality of staples ejectable from the reload by the transmission assembly.

5. The surgical device according to claim 4, wherein the reload further includes a cutting assembly.

6. The surgical device according to claim 5, wherein completing the process includes advancing the transmission assembly and at least one of ejecting the plurality of staples or advancing the cutting assembly.

7. The surgical device according to claim 6, wherein terminating the process includes retracting the transmission assembly.

8. The surgical device according to claim 1, wherein the sensor includes a strain gauge.

9. The surgical device according to claim 8, wherein the strain gauge is configured to measure force imparted on the transmission assembly.

10. A surgical device comprising:
a power source;
a motor coupled to the power source;
a reload including a plurality of staples ejectable from the reload and a cutting assembly;
a stapling transmission assembly movable by the motor to eject the plurality of staples;
a cutting transmission assembly movable by the motor to advance the cutting assembly;
a sensor configured to monitor operation of the stapling transmission assembly and the cutting transmission assembly and to output sensor data;
a controller configured to:
determine position of the stapling transmission assembly and the cutting transmission assembly;
operate the motor to move the stapling transmission assembly based on the position of the stapling transmission assembly and an interruption in the sensor data; and
operate the motor to move the cutting transmission assembly based on the position of the cutting transmission assembly and an interruption in the sensor data.

11. The surgical device according to claim 10, wherein the controller is further configured to:
operate the motor to complete a stapling process in response to the position of the stapling transmission assembly being at or beyond a threshold position.

12. The surgical device according to claim 11, wherein completing the process includes advancing the stapling transmission assembly to eject the plurality of staples.

13. The surgical device according to claim 11, wherein the controller is further configured to:
operate the motor to terminate the stapling process in response to the position of the stapling transmission assembly being below the threshold position and the interruption in the sensor data.

14. The surgical device according to claim 13, wherein terminating the process includes retracting the stapling transmission assembly.

15. The surgical device according to claim 10, wherein the controller is further configured to:
operate the motor to complete a cutting process in response to the position of the cutting transmission assembly being at or beyond a threshold position.

16. The surgical device according to claim 15, wherein completing the process includes advancing the cutting transmission assembly to advance the cutting assembly.

17. The surgical device according to claim 15, wherein the controller is further configured to:
operate the motor to terminate the cutting process in response to the position of the cutting transmission assembly being below the threshold position and the interruption in the sensor data.

18. The surgical device according to claim 17, wherein terminating the process includes retracting the cutting transmission assembly.

19. The surgical device according to claim 10, wherein the sensor includes a strain gauge.

20. The surgical device according to claim 19, wherein the strain gauge is configured to measure force imparted on the stapling transmission assembly and the cutting transmission assembly.

* * * * *